United States Patent [19]

Himmelsbach et al.

[11] Patent Number: 6,136,866
[45] Date of Patent: Oct. 24, 2000

[54] PREPARATION FOR REDUCING THE BOND STRENGTH OF ADHESIVE TAPES

[75] Inventors: Peter Himmelsbach, Buxtehude; Hanns Pietsch; Roland Knieler, both of Hamburg, all of Germany

[73] Assignee: Beiersdorf AG, Hamburg, Germany

[21] Appl. No.: 09/021,334

[22] Filed: Feb. 10, 1998

[30] Foreign Application Priority Data

Mar. 14, 1997 [DE] Germany .......................... 197 10 543

[51] Int. Cl.[7] .............................. A61L 15/50; A61L 15/58
[52] U.S. Cl. ............................ 514/762; 514/506; 514/715
[58] Field of Search .................................. 514/762, 715, 514/536, 537, 947, 506

[56] References Cited

U.S. PATENT DOCUMENTS

| | | | |
|---|---|---|---|
| 4,867,981 | 9/1989 | Grof | 424/443 |
| 5,156,846 | 10/1992 | Petersen et al. | 424/443 |
| 5,470,563 | 11/1995 | Tanaka et al. | 424/448 |
| 5,759,584 | 6/1998 | Traupe et al. | 424/520 |
| 5,803,639 | 9/1998 | Gusakov et al. | 401/139 |

FOREIGN PATENT DOCUMENTS

826380 A2  3/1998  European Pat. Off. .

*Primary Examiner*—Robert H. Harrison
*Attorney, Agent, or Firm*—Norris, McLaughlin & Marcus, P.A.

[57] ABSTRACT

Preparation for reducing the bond strength of adhesive tapes, consisting of at least one penetrant and at least one bond strength-reducing active substance which is skin-compatible and may make an active contribution to skincare, where the bond strength-reducing active substance contains at least one hydrocarbon chain of the form ($C_nH_m$) where n is the number of carbon atoms in the chain and has a value of greater than 6, and where the adhesive-reducing [sic] active substance has a primary irritation index of less than 3, with particular preference 0.

13 Claims, No Drawings

PREPARATION FOR REDUCING THE BOND STRENGTH OF ADHESIVE TAPES

The invention relates to a preparation for the nondestructive and residueless detachment of adhesive tapes, especially medical plaster.

Strongly adhering plasters, especially orthopaedic bandages, are generally difficult to detach after use. In some cases detachment is accompanied by mechanical injury to the skin or by epilation. To enable painless detachment so-called tape removers are employed. These facilitate detachment but are of only limited effect for specific adhesive systems.

Regular use of the known systems on skin may have an adverse effect, since it leads to the skin drying out. Tape removers known to date have little if any skincare effect.

A system is generally desired to possess not only functionality, in other words effectiveness, but also a rapid action and ease of metering. For orthopaedic bandages in particular it is necessary for the tape remover to act even through several layers of adhesive strips.

Since [lacuna] orthopaedic bandages in particular, such as, for example, in the case of functional tape dressings, the dressing is removed to change the dressing, it is also absolutely necessary that the active substance, immediately following the removal of the dressing, does not hinder renewed sticking with a new strip.

Tape removers for adhesive systems based on Zn-rubber adhesive compositions are on the market. Disadvantages of these tape removers are that they are not skincare-active and are not suitable for all adhesive systems, especially for specific hotmelt adhesive compositions based on block copolymers.

J0173437 A describes a compound based on an R-COOR1 fatty acid ester which is dispersed in organic solvents, at least one group having a long alkyl hydrocarbon chain. In the case of this system the selection of the active substance already greatly restricts the functionality for universal use on various adhesive systems.

DE P 16 69 304.2 describes a process for the residueless detachment of plasters and other adhesive products. The examples given, however, contain no skincare substance and in some cases must even nowadays be classified as damaging to health. The preferred active constituents are amides and sulphoxides. No skincare property has been described, nor the universal action on various adhesive systems.

U.S. Pat. No. 4 867 981 likewise describes a composition which detaches adhesive tape and which is composed of various hydrophilic and hydrophobic constituents. No skincare property has been described, nor the universal action on various adhesive systems.

The object of the invention was to provide a preparation for reducing the bond strength, which does not have the disadvantages known to the prior art and which, in particular, has a skincare action.

This object is achieved by means of a preparation as is described in claim 1. Advantageous embodiments are the subject of the subclaims.

Accordingly, the preparation for reducing the bond strength of adhesive tapes consists of at least one penetrant and at least one bond strength-reducing active substance which is skin-compatible and may make an active contribution to skincare, where the bond strength-reducing active substance contains at least one hydrocarbon chain of the form $(C_nH_m)$ where n is the number of carbon atoms in the chain and has a value of greater than 6, and where the adhesive-reducing [sic] active substance has a primary irritation index of less than 3, with particular preference 0.

In a preferred embodiment of the invention the active substance has a $H_{50}$ value of greater than 1000 mg/L, preferably greater than 3000 mg/L and, with particular preference, greater than 10,000 mg/L.

The content of the active substance in the preparation is preferably less than 99% by weight, more preferably less than 50% by weight and, with particular preference, from 0.01% by weight to 10% by weight.

The active substance is, furthermore, preferably a hydrocarbon, more preferably a hydrocarbon oil or paraffin, an ether, an alcohol, especially tetradecanol or hexadodecanol, an ester having at least one aromatic group, or a triglyceride.

Preferably, the preparation of the invention reduces the bond strength of an adhesive strip on steel or on skin by at least 30%. This permits the nondestructive or, respectively, the painless and non-epilative detachment of the adhesive strip.

In addition, the constituents of the preparation of the invention are selected so that even in the case of a multi-ply use they are able to penetrate down to the substrate. This is preferably achieved by a specific adjustment of the viscosity of the preparation and/or of the active substance. In this case both a preparation with Newtonian flow and a preparation with non-Newtonian flow may be advantageous depending on the particular case. Mention is made here by way of example of the pseudoplastic or plastic, the tixotropic [sic] and rheopexic flow behaviour for such preparations. The same applies to the active substance.

It is advantageous if the viscosity $\eta$ which results for the use of the preparation, at a temperature of 25° C. and a shear rate of $1*1/s$, is less than 10 Pas, preferably less than 1 Pas.

For the metering of the preparation it has been found, moreover, that preparations having a plastic flow behaviour can be applied more simply and without losses than preparations without plastic flow behaviour. The flow limit $\tau_{crit}$ and the critical viscosity $\eta_{crit}$ are advantageously chosen so that even in the case of a multi-ply use they are able to penetrate down to the substrate. It has been found advantageous here that the critical $\eta_{crit}$ at a temperature of 25° C. is always less than $5.0*10^4$ Pas and the shear stress at $\eta_{crit}$ and 25° C. is always smaller than 25 Pa. Particular preference is given to preparations where at a temperature of 25° C. the critical viscosity $\eta_{crit}$ is always lower than $2*10^4$ Pas and the shear stress $\tau_{crit}$ at $\eta_{crit}$ and 25° C. is always less than 15 Pa.

Gentle rubbing-in of such a preparation then lowers the viscosity so that penetration through the layers of adhesive tape is possible.

Quite a few methods have been described scientifically for the testing of skin compatibility. This applies also to the active skincare of substances or mixtures. A description will be given below, by way of example, of only two methods, the HET test and RBC test.

In the HET test (Horst Spielmann et al, Results of Validation Study in Germany on Two In Vitro Alternatives to the Draize Eye Irritation, the HET-CAM Test and the 3T3 NRU Cytotoxity Test, ALTA 24, 741–858, 1996) pretreated hen's eggs are brought together in a specific manner with the corresponding active substances or preparations.

Following a fixed period after the application, the moments of onset of three types of reaction are determined. They lead, by way of an empirical formula, to the primary irritation indices, a classification of the active substances or preparations. Highly irritant substances have a high primary irritation index. A preparation or substance causing little or no irritation possess [sic] a primary irritation index of less than three.

Through the RBC test according to Pape et. [sic] al. and Balls et. [sic] al. (Pape W. J. W. et al; Validation of the red blood cell test system as in vitro assay for the rapid screening of irritation potentials of surfactants, Mol Toxical. [sic] 1987; 1, 525–536; Balls M. et al, The EC/HO International Validation Study on Alternatives to the Eye Irritation Test; Toxicology in vitro, 1995, 9, 871–929) it is likewise possible to determine irritation potentials. In this case, in a series with ascending concentration, the preparations or active substances to be investigated are is [sic] incubated with a defined aliquot of isolated calf erythrocytes and analysed. The degree of haemolysis resulting from this allows calculation of the $H_{50}$ value (mg/L), i.e. the concentration at which 50% of the haemoglobin have been released.

If this $H_{50}$ value is greater than 1000 mg/L, preferably greater than 3000 mg/L and, with particular preference, greater than 10,000 mg/L, the irritation potential is classified as low.

The proportion of all substances which have an irritation potential in the preparation should always be lower than 300 mg/kg, preferably 200 mg/kg.

The intention below is to illustrate the preparation of the invention by means of a number of examples without thereby intending unnecessarily to restrict the subject-matter of the invention.

EXAMPLE 1

Composition:

TABLE 1

Composition of Preparation 1

|   | substance | amount [g] | designation |
|---|---|---|---|
| 1 | ethanol | 96 | |
| 2 | benzinium DAB* 10 Fischar, Saarbrücken | 2 | |
| 3 | myristyl alcohol | 2 | tetradecanol |

*DAB = German Pharmacopoeia

Preparation 1 was prepared in a glass beaker. This was done by adding the tetradecanol to the benzinium and then adding the ethanol dropwise to the mixture with continuous stirring.

The preparation prepared in this way had a viscosity η of η=2.95⁸10⁻³ Pas at a temperature of 25° C. and a shear rate of 100*1/s. It therefore had a quasi-Newtonian flow behaviour.

The tetradecanol had an $H_{50}$ value of about 190 mg/L.

In order to ascertain the reduction in the bond strength of adhesive tapes which is achievable by means of Preparation 1, backing materials with a self-adhesive coating were investigated. The adhesive compositions used for this purpose were acrylate adhesives, adhesives based on Zn-rubber and based on SEBS block copolymers.

First of all, the backing materials with a self-adhesive coating, in the form of sections having an area of 2 cm×5 cm, were bonded to steel. The sections were then coated with the preparation of the invention, i.e. in this case Preparation 1. After a period of action of 10 seconds the bond strengths of the sections to steel were measured, specifically by the 180° method. This had been preceded by measurement of the bond strengths of identical sections to steel by the 180° method without the use of a preparation.

The values measured are set out in Table 2 which follows.

TABLE 2

Results for bond strength to steel by 180° method with Preparation 1

| backing materials coated with | bond strength without tape remover [N/cm] | bond strength with tape remover [N/cm] |
|---|---|---|
| SEBS hotmelt adhesive | 4.4 | 0.16 |
| Zn-rubber adhesive | 3.8 | 0.9 |
| acrylate adhesive | 1.8 | 0.7 |

Accordingly, Preparation 1 reduced the bond strength to steel by at least 30%, with the greatest reduction being achievable in the case of backing materials that were coated with an SEBS hotmelt adhesive.

The same applied to backing material sections which were stuck on the skin of test subjects.

Furthermore, the skin showed no irritation even after ten applications. At the same time there was no partial dissolution of the adhesive composition, nor any transfer of the adhesive composition to the skin. With all of the backing materials having a self-adhesive coating it was possible to stick the sections again to the same areas of skin.

The subjective perception of test subjects awarded Preparation 1 a cooling care action.

EXAMPLE 2

Composition:

TABLE 3

Composition of Preparation 2

|   | substance | amount [g] | designation |
|---|---|---|---|
| 1 | water | 30 | |
| 2 | 2-isopropanol | 35 | |
| 3 | Finsolv TN, Witco | 35 | $C_{12}$–$C_{15}$-alkyl benzoate |

Preparation 2 was prepared in a glass beaker. This was done by adding the Finsolv TN to the 2-isopropanol and then adding the water dropwise to the mixture with continuous stirring.

The $C_{12}$–$C_{15}$-alkyl benzoate has an irritation index of 0.

In accordance with Example 1, in Example 2 as well an identical series of experiments was carried out with the Preparation 2 and variously coated backing materials.

The results obtained were as follows:

TABLE 4

Results for bond strength to steel by 180° method with Preparation 2

| backing materials coated with | bond strength without tape remover [N/cm] | bond strength with tape remover [N/cm] |
|---|---|---|
| SEBS hotmelt adhesive | 4.4 | 0.16 |
| Zn-rubber adhesive | 3.7 | 1.2 |
| acrylate adhesive | 1.82 | 0.9 |

Accordingly, Preparation 2 reduced the bond strength to steel actually by up to 95%, with the greatest reduction again being achievable in the case of backing materials having an SEBS hotmelt adhesive composition.

The same applied to backing material sections which were stuck on the skin of test subjects.

Furthermore, the skin showed no irritation even after ten applications. At the same time there was no partial dissolution of the adhesive composition, nor any transfer of the adhesive composition to the skin. With all of the backing materials having a self-adhesive coating it was possible to stick the sections again to the same areas of skin.

The subjective perception of test subjects awarded Preparation 2 a cooling, smoothing care action.

EXAMPLE 3

Composition:

TABLE 5

Composition of Preparation 3

| | substance | amount [g] | designation |
|---|---|---|---|
| 1 | water | 84.7 | |
| 2 | ethanol | 5 | |
| 3 | Finsolv TN, Witco | 5 | $C_{12}$–$C_{15}$-alkyl benzoate |
| 4 | Eutanol G, Henkel KG aA | 3 | 2-octyldodecanol |
| 5 | isohexadecane, EC Erdölchemie GmbH | 2 | $C_{16}$–$C_{20}$ isoparaffins |
| 6 | Carbopol, Goodrich | 0.3 | polyacrylic acid, NaOH |

Preparation 3 was prepared by combining isohexadecane, Finsolv TN, Eutanol G and Carbopol in an open stirred vessel. The mixture of ethanol and water, prepared in parallel, was added dropwise to the stirred vessel at 80° C.

The substances were subsequently stirred together in an homogenizer until a homogeneous mixture had been prepared.

The active substances were employed in a mixture. Isohexadecane, Finsolv TN, Eutanol G had an irritation index of 0.

Preparation 3 showed plastic flow behaviour; the critical flow viscosity was $\eta_{crit}=1.04*10^4$ Pas, the critical shear stress $\tau_{crit}=10$ Pa.

Preparation 3 penetrated the backing materials prepared in accordance with Example 1, with a self-adhesive coating, in less than 30 seconds.

The results obtained were as follows:

TABLE 6

Results for bond strength to steel by 180° method with Preparation 3

| backing materials coated with | bond strength without tape remover [N/cm] | bond strength with tape remover [N/cm] |
|---|---|---|
| SEBS hotmelt adhesive | 4.4 | 1.8 |
| Zn-rubber adhesive | 3.7 | 1.8 |
| acrylate adhesive | 1.82 | 1.3 |

Accordingly, Preparation 3 reduced the bond strength to steel by up to 65%, the greatest reduction again being found in the case of SEBS hotmelt adhesive composition.

The same applied to backing material sections which were stuck on the skin of test subjects.

Furthermore, the skin showed no irritation even after ten applications. At the same time there was no partial dissolution of the adhesive composition, nor any transfer of the adhesive composition to the skin. With all of the backing materials having a self-adhesive coating it was possible to stick the sections again to the same areas of skin.

The subjective perception of test subjects awarded Preparation 3 a cooling, smoothing care action.

What is claimed is:

1. Preparation for reducing the bond strength of adhesive tapes, comprising at least one penetrant and at least one bond strength-reducing, skin-compatible active substance, wherein said bond strength-reducing, skin-compatible active substance is selected from the group consisting of hydrocarbon oils, paraffins, alcohols, esters having at least one aromatic group and triglycerides, each of which bond strength-reducing, skin-compatible active substance has at least one hydrocarbon chain which has more than 6 carbon atoms and wherein said bond strength-reducing active substance has a primary irritation index of less than 3.

2. Preparation according to claim 1, wherein the bond strength-reducing active substance has an $H_{50}$ value greater than 1000 mg/L.

3. Preparation according to claim 1, wherein the content of the bond strength-reducing active substance in the preparation is less than 99% by weight.

4. Preparation according to claim 1, wherein the bond strength of said adhesive tapes to steel and to skin is reduced by at least 30%.

5. Preparation according to claim 1, wherein the bond strength-reducing active substance, the preparation, or both, have Newtonian, pseudoplastic, structurally viscous or thixotropic flow properties.

6. Preparation according to claim 1, wherein the preparation has a viscosity $\eta$ of less than 10 Pas at a temperature of 25° C. and a shear rate of $1*1/s$.

7. Preparation according to claim 1, wherein the preparation has a critical viscosity $\eta_{crit}$ of less than $5.0*10^4$ Pas at a temperature of 25° C. and a shear stress $\tau_{crit}$ of less than 25 Pa at $\eta_{crit}$ and 25° C.

8. Preparation according to claim 2, wherein said $H_{50}$ value is greater than 3000 mg/L.

9. Preparation according to claim 2, wherein said $H_{50}$ value is greater than 10,000 mg/L.

10. Preparation according to claim 3, wherein said content of bond strength-reducing active substance is less than 50% by weight.

11. Preparation according to claim 3, wherein said content of bond strength-reducing active substance is from 0.01% by weight to 10% by weight.

12. Preparation according to claim 6, wherein said critical viscosity $\eta_{crit}$ is less than $2.0*10^4$ Pas.

13. Preparation according to claim 6, wherein said shear stress $\tau_{crit}$ is less than 15 Pa.

* * * * *